US009797823B2

(12) United States Patent
Yamasaki et al.

(10) Patent No.: US 9,797,823 B2
(45) Date of Patent: Oct. 24, 2017

(54) PURIFIED WATER MANUFACTURING DEVICE MONITORING SYSTEM AND PURIFIED WATER MANUFACTURING DEVICE MONITORING METHOD

(71) Applicant: Azbil Corporation, Tokyo (JP)

(72) Inventors: Shinsuke Yamasaki, Tokyo (JP); Daisuke Obara, Tokyo (JP); Masashi Furuya, Tokyo (JP)

(73) Assignee: AZBIL CORPORATION, Tokyo (JP)

( * ) Notice: Subject to any disclaimer, the term of this patent is extended or adjusted under 35 U.S.C. 154(b) by 215 days.

(21) Appl. No.: 14/722,596

(22) Filed: May 27, 2015

(65) Prior Publication Data

US 2015/0346072 A1 Dec. 3, 2015

(30) Foreign Application Priority Data

May 27, 2014 (JP) .................. 2014-109477

(51) Int. Cl.
*G01N 21/00* (2006.01)
*G01N 15/06* (2006.01)
(Continued)

(52) U.S. Cl.
CPC ............. *G01N 15/06* (2013.01); *C02F 1/008* (2013.01); *G01N 33/18* (2013.01);
(Continued)

(58) Field of Classification Search
CPC .. G02B 1/043; G02B 2207/109; G02B 21/32; G02B 6/00; G02B 6/0036; G02B 6/0043;
(Continued)

(56) References Cited

U.S. PATENT DOCUMENTS 6,885,440 B2   4/2005   Silcott et al.
7,106,442 B2   9/2006   Silcott et al.
(Continued)

FOREIGN PATENT DOCUMENTS

JP        2997099 B2    1/2000
JP     2001-327967 A   11/2001
(Continued)

*Primary Examiner* — Michael P Stafira
(74) *Attorney, Agent, or Firm* — Oblon, McClelland, Maier & Neustadt, L.L.P.

(57) ABSTRACT

A purified water manufacturing device monitoring system includes: a detecting device that illuminates, with an inspection beam, water either that is in a process of being manufactured or that has been manufactured by a purified water manufacturing device, detects light in a region illuminated by the inspection beam, and detects a microorganism or a non-microorganism particle included in the water; a measured value specifying portion that specifies a measured value for a number of microorganisms detected and specifies a measured value for a number of non-microorganism particles detected; and a state evaluating portion that evaluates that a problem has occurred in the purified water manufacturing device when either or both the measured value for the number of microorganisms and the measured value for the number of non-microorganism particles are greater than a prescribed value.

22 Claims, 8 Drawing Sheets

(51) Int. Cl.
  *C02F 1/00* (2006.01)
  *G01N 33/18* (2006.01)
  *C02F 103/02* (2006.01)

(52) U.S. Cl.
  CPC .... *C02F 2103/026* (2013.01); *C02F 2209/36* (2013.01); *C02F 2303/04* (2013.01); *G01N 2015/0693* (2013.01)

(58) Field of Classification Search
  CPC ............... G02B 6/06; G01N 15/1456; G01N 2015/1497; G01N 2015/0693; G01N 2520/00; G01N 33/56916; G01N 15/0227; G01N 15/1434
  See application file for complete search history.

(56) References Cited

U.S. PATENT DOCUMENTS

| | | | | |
|---|---|---|---|---|
| 2003/0090657 | A1* | 5/2003 | Drake | G01N 15/1456 356/338 |
| 2008/0030730 | A1* | 2/2008 | Clark | G01N 21/49 356/338 |
| 2009/0046287 | A1* | 2/2009 | Haught | G01J 3/02 356/319 |
| 2009/0266762 | A1 | 10/2009 | Ito et al. | |
| 2010/0097605 | A1* | 4/2010 | Murakami | B01D 61/20 356/337 |
| 2011/0102790 | A1* | 5/2011 | Haught | G01J 3/02 356/319 |
| 2013/0321800 | A1* | 12/2013 | Margalit | G01J 3/44 356/301 |
| 2015/0077756 | A1* | 3/2015 | Campbell | G01N 33/1826 356/450 |

FOREIGN PATENT DOCUMENTS

| | | |
|---|---|---|
| JP | 2003-260463 A | 9/2003 |
| JP | 2007-093209 A | 4/2007 |
| JP | 2007-252978 A | 10/2007 |
| JP | 2008-107244 A | 5/2008 |
| JP | 2008-111721 A | 5/2008 |
| JP | 2012-192315 A | 10/2012 |
| WO | 2008/038575 A1 | 4/2008 |

* cited by examiner

PURIFIED WATER MANUFACTURING DEVICE MONITORING SYSTEM AND PURIFIED WATER MANUFACTURING DEVICE MONITORING METHOD

CROSS REFERENCE TO RELATED APPLICATION

This application claims priority under 35 U.S.C. §119 to Japanese Patent Application No. 2014-109477, filed on May 27, 2014, the entire content of which being hereby incorporated herein by reference.

FIELD OF TECHNOLOGY

The present invention relates to a quality evaluating technology, relating to a purified water manufacturing device monitoring system and a purified water manufacturing device monitoring method.

BACKGROUND

In water wherein there are control limit values, such as purified water, water for pharmaceutical manufacturing, water for infusions, and the like, treatment reference values for microorganisms have been established in the Pharmacopeia. These waters are manufactured through purified water manufacturing equipment that uses, for example, the ultrafiltration method, the reverse osmosis membrane method, the precision filtration membrane method, or the like. See, for example, Japanese Unexamined Patent Application Publication Nos. 2003-260463, 2012-192315 and 2007-093209, Japanese Patent No. 2997099, and International Patent Application Publication No. 2008/038575.

During manufacturing, quality of these waters, such as purity, is controlled through monitoring electric conductivity and TOC (Total Organic Carbon), or fluorescent intensity. See, for example, Japanese Unexamined Patent Application Publication Nos. 2008-107244, 2008-111721, 2001-327967, and 2007-252978. Moreover, after these waters are manufactured, a portion of the water is extracted and inoculated into a culture medium to examine the number of colonies of the microorganisms that are produced under specific conditions. Whether or not microorganisms in the water that has been manufactured are below the treatment standard values is inspected thereby.

However, insoluble microorganisms and non-microorganism particles clog filters of purified water manufacturing devices or, even if they pass through the filters so that the water contains insoluble microorganisms and non-microorganism particles, there will be no change in electrical conductivity of the water. Moreover, often microorganisms and non-microorganism particles are easily oxidized, so detection with TOC meters is also difficult. Furthermore, even simple measurements of fluorescent intensity of water cannot identify the types of substances included in the water.

Additionally, detection of amount of suspended materials and soluble organic carbon quantities, and observations of the shapes of biofilms, are after the purified water manufacturing device is contaminated with a substantial quantity of microorganisms or non-microorganism particles. Because of this, it is difficult to discover quickly the inclusion of microorganisms and non-microorganism particles in water wherein high purity levels are required. Furthermore, discovering a large number of microorganism colony structures after the water is manufactured makes it necessary to trace back the manufacturing date to handle the purified water, which is wasteful in terms of manufacturing costs and time.

Given this, an aspect of the present invention is to provide a monitoring system and monitoring method that can monitor a purified water manufacturing device accurately and in real time.

SUMMARY

One aspect of the present invention provides a purified water manufacturing device monitoring system comprising: (a) a detecting device for illuminating, with an inspection beam, water that is being manufactured or that has been manufactured by the purified water manufacturing device, to detect light that is produced in a region that is illuminated by the inspection beam, to detect microorganism and non-microorganism particles that are included in the water; (b) a measured value specifying portion for specifying a measured value for the number of microorganisms detected and a measured value for the number of non-microorganism particles detected; and (c) a state evaluating portion for evaluating that a problem has occurred in the purified water manufacturing device if the measured value for the number of microorganisms and/or the measured value for the number of non-microorganism particles is greater than a prescribed value.

Moreover, one aspect of the present invention provides a purified water manufacturing device monitoring method including: (a) illuminating, with an inspection beam, water that is being manufactured or that has been manufactured by the purified water manufacturing device, to detect light that is produced in a region that is illuminated by the inspection beam, to detect microorganism and non-microorganism particles that are included in the water; (b) specifying a measured value for the number of microorganisms detected and a measured value for the number of non-microorganism particles detected; and (c) evaluating that a problem has occurred in the purified water manufacturing device if the measured value for the number of microorganisms and/or the measured value for the number of non-microorganism particles is greater than a prescribed value.

This makes it possible to provide a monitoring system and monitoring method able to monitor a purified water manufacturing device accurately and in real time.

BRIEF DESCRIPTIONS OF THE DRAWINGS

DETAILED DESCRIPTION

Examples of the present disclosure will be described below. In the descriptions of the drawings below, identical or similar parts are expressed by identical or similar codes. Note that the diagrams are schematic. Consequently, specific measurements should be evaluated in light of the descriptions below. Furthermore, even within these drawings there may, of course, be portions having differing dimensional relationships and proportions.

Example

Figure 1:
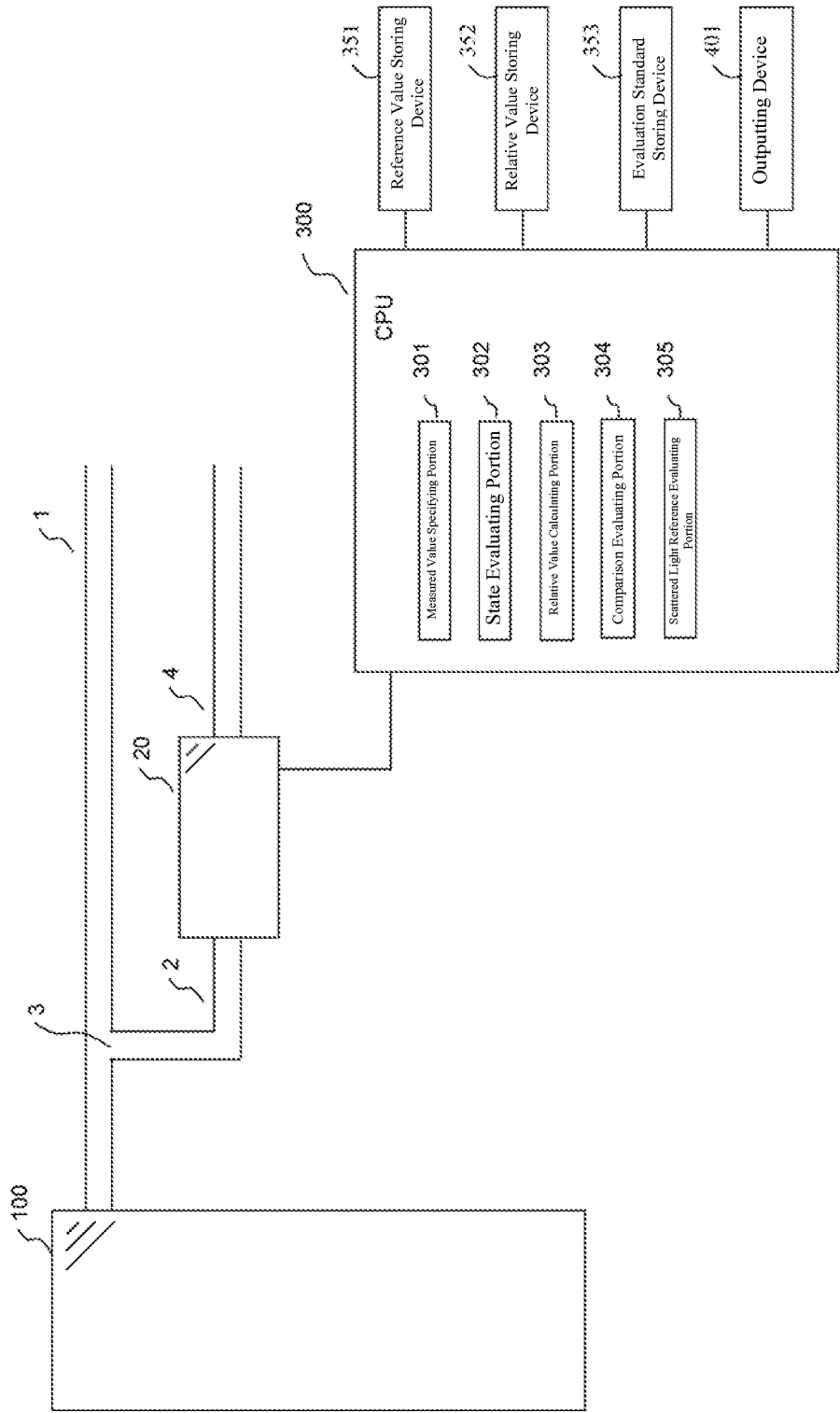
FIG. 1 is a schematic diagram of a purified water manufacturing apparatus monitoring system as set forth in Example according to the present disclosure.

As illustrated in FIG. 1, a purified water manufacturing device monitoring system according to Example according to the present invention comprises: a detecting device 20 for illuminating, with an inspection beam, water that is being manufactured by a purified water manufacturing device 100 or water that has been manufactured by the purified water manufacturing device 100, to detect light that is produced in a region that is illuminated by the inspection beam, to detect microorganism and non-microorganism particles that are included in the water; a measured value specifying portion 301 for specifying a measured value for the number of microorganisms detected and a measured value for the number of non-microorganism particles detected; and a state evaluating portion 302 for evaluating that a problem has occurred in the purified water manufacturing device if the measured value for the number of microorganisms and/or the measured value for the number of non-microorganism particles is greater than a prescribed value. The measurement value specifying portion 301 and status evaluating portion 302 are included in, for example, a central calculating processing unit (CPU) 300. Here particles of abiotic substances include, for example, non-toxic or toxic chemical substances, and various types of dust, and the like. Moreover, in the present disclosure, the expressions "greater than" and "more than" include also "at least."

The purified water manufacturing device 100 includes, for example, and ultrafiltration membrane, a reverse osmosis membrane, or a precision filtration membrane, or the like. The water that is being manufactured by the purified water manufacturing device 100 or water that has been manufactured by the purified water manufacturing device 100 flows through a main pipe 1. A branch pipe 2 is connected to the main pipe 1 through a sampling pipe 3. A portion of the water that flows through the main pipe 1 flows into the branch pipe 2. The water during manufacturing by the purified water manufacturing apparatus 100, or the purified water that has been manufactured by the purified water manufacturing apparatus 100, is, for example, pure water, water for pharmaceutical manufacturing, water for infusion, and the like, although there is no limitation thereto. The detecting device 20 is provided in the branch pipe 2. As a result, a portion of the water is introduced into the detecting device 20 from the main pipe 1 wherein the water is flowing.

Figure 2:
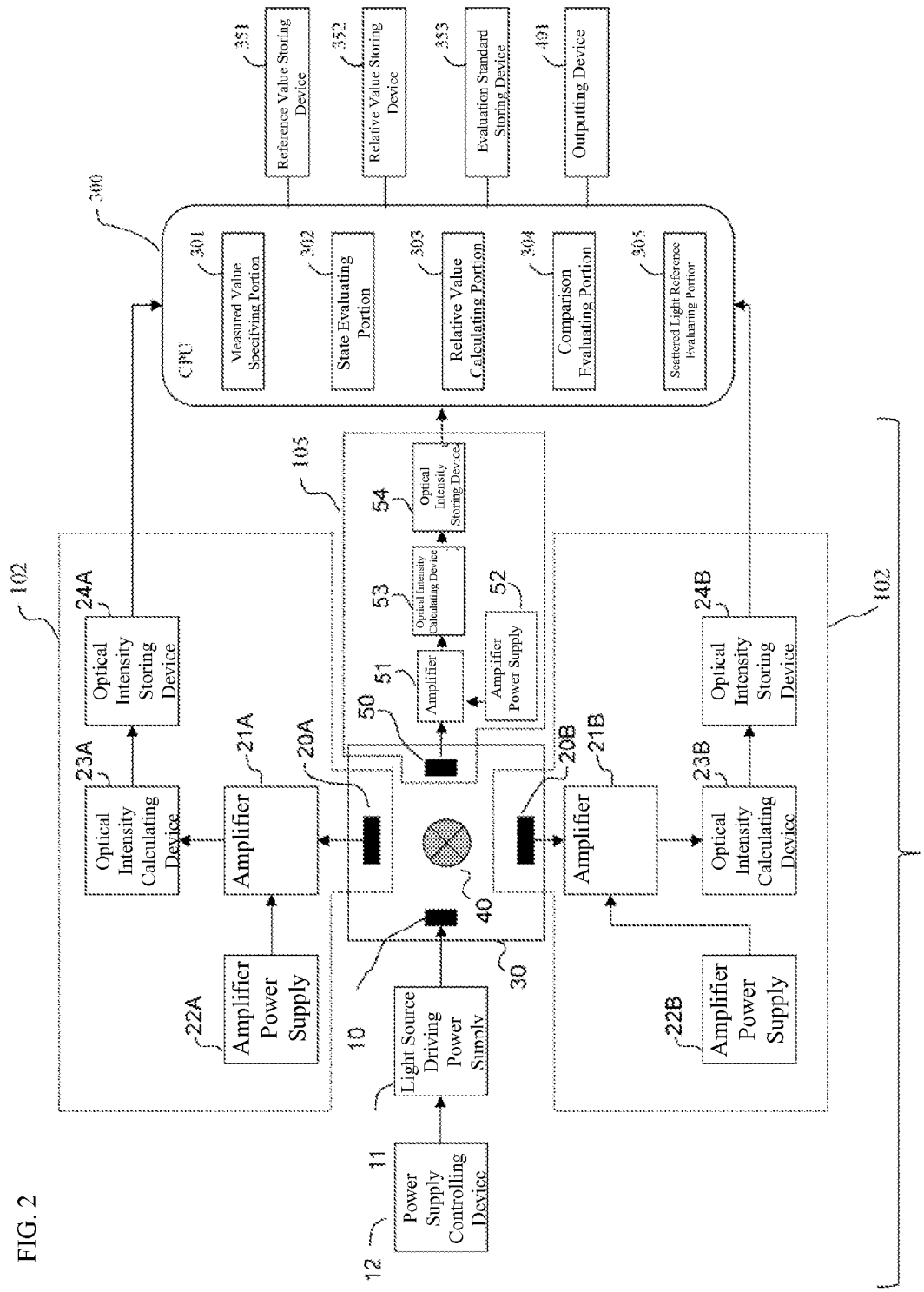
FIG. 2 is a schematic diagram of a detecting device as set forth in the Example according to the present disclosure.

The detecting device 20, as illustrated in FIG. 2, comprises, for example, a light source 10 for illuminating water with an inspection beam, a fluorescent intensity measuring instrument 102 for measuring the light intensity in the fluorescent band, produced in the region illuminated by the inspection beam, at at least two wavelengths, and a scattered light measuring instrument 105 for measuring scattered light produced in the region illuminated by the inspection beam. The light source 10, the fluorescent intensity measuring instrument 102, and the scattered light measuring instrument 105 are connected electrically to a CPU 300.

The CPU 300 includes a relative value calculating portion 303 for calculating relative value for the light intensities in the fluorescent band measured at at least two wavelengths. The CPU 300 is connected electrically to a reference value storing device 351 for storing, as reference values, relative values for the light intensity in the fluorescent band produced by prescribed substances illuminated with the inspection beam and the measured at at least two wavelengths. The CPU 300 includes a comparison evaluating portion 304 for comparing the relative value calculated by the relative value calculating portion 303 to the reference values stored in the reference value storing device 351, to evaluate whether a particle that is detected is a microorganism, a non-microorganism particle, or a bubble.

Here the "relative value of light intensities measured at at least two wavelengths" is, for example, a ratio of a light intensity at a first wavelength and a light intensity at a second wavelength that is other than the first wavelength, or the ratio of the difference between the light intensity at the first wavelength and the light intensity at the second wavelength to the sum of the light intensity at the first wavelength and the light intensity at the second wavelength, or the difference between the light intensity at the first wavelength and the light intensity at the second wavelength.

The light source 10, the fluorescence intensity measuring instrument 102, and the scattered light measuring instrument 105 are provided in the frame 30. A light source driving power supply 11 for supplying electric power to the light source 10 is connected to the light source 10. A power supply controlling device 12 for controlling the electric power that is supplied to the light source 10, is connected to the light source driving power supply 11. The water that is being manufactured by the purified water manufacturing device 100 or water that has been manufactured by the purified water manufacturing device 100, obtained from a branch flow pipe 2, illustrated in FIG. 1, flows in a clear cell 40, illustrated in FIG. 2. The water that flows through the cell 40 is expelled into a drain pipe 4, illustrated in FIG. 1.

The light source 10 illustrated in FIG. 2 directs an inspection beam of a broadband wavelength toward the water flow in the cell 40. A light-emitting diode (LED) or a laser, for example, may be used as the light source 10. The wavelength of the inspection beam is, for example, between 250 and 550 nm. The inspection beam may be visible light or may be ultraviolet light. If the inspection beam is visible light, then the wavelength of the inspection beam is in a range of, for example, between 400 and 550 nm, such as, for example, 405 nm. If the inspection beam is ultraviolet light, then the wavelength of the inspection beam is in a range of, for example, between 300 and 380 nm, for example, 340 nm. Note that the wavelength of the inspection beam is not limited to these.

If the water flowing in the cell 40 includes a microorganism, such as a bacterium, then the nicotinamide adenine nucleotides and riboflavin, and the like, included in the microorganism that is illuminated by the inspection beam, as an excitation beam, will emit fluorescence. Moreover, if, for example, a non-microorganism particle made from, for example, metal or resin is included in the water flow in the cell 40, the non-microorganism particle that is illuminated with the inspection beam may fluoresce or may emit light in a wavelength band that overlaps fluorescence.

For example, the water that has been manufactured by the purified water manufacturing device 100 may include non-microorganism particles made from a component material of the purified water manufacturing device 100. For example, particles comprising materials such as polypropylene, polyethylene, poltetrafluoroethylene (PTFE), olefin, polycarbonate, and/or polyurethane may be produced from the filter or housing within the purified water manufacturing device 100. Particles of materials such as silicon rubber, nitrile rubber (NBR), ethylene polypropylene rubber (EPDM), fluorine rubber, kalrez, and/or PTFE, or the like, may be produced from the packings in the purified water manufacturing device 100. Particles of Viton, fluorine resin, silicon resin, polyamide, polyphenylene sulfide (PPS) and/or perfluoro may be produced from the pump that is included in the purified water manufacturing device 100. Particles of, for example, PTFE, or the like, may be produced from seals that may be provided in the purified water manufacturing device 100. Particles of metal materials, such as oxidized stainless steel, and the like, may be produced from piping that is provided in the purified water manufacturing device 100. The materials of the particles that are produced by the purified water manufacturing device 100, as described above, when illuminated with an excitation beam, may fluoresce or may emit light having a wavelength band that overlaps fluorescence.

The fluorescence intensity measuring instrument 102 detects light in the fluorescent band produced by the microorganisms and the non-microorganism particles. The fluorescent intensity measuring instrument 102 comprises a first photodetecting element 20A for detecting light in the fluorescent band at a first wavelength, and a second photodetecting element 20B for detecting light in the fluorescent band at a second wavelength other than the first wavelength. Note that the first wavelength may have a band. This is true for the second wavelength as well. Photodiodes, photoelectron tubes, and the like, may be used for the first photodetecting element 20A and the second for detecting element 20B, to convert optical energy into electrical energy when light is detected.

An amplifier 21A for amplifying the electric current that is produced by the first photodetecting element 20A is connected to the first photodetecting element 20A. An amplifier power supply 22A for supplying electric power to the amplifier 21A is connected to the amplifier 21A. Moreover, an optical intensity calculating device 23A, for inputting the current that has been amplified by the amplifier 21A to calculate the intensity of the light detected by the first photodetecting element 20A, is connected to the amplifier 21A. An optical intensity storing device 24A for saving the optical intensity calculated by the optical intensity calculating device 23A is connected to the optical intensity calculating device 23A.

An amplifier 21B for amplifying the electric current that is produced by the second photodetecting element 20B is connected to the second photodetecting element 20B. An amplifier power supply 22B for supplying electric power to the amplifier 21B is connected to the amplifier 21B. Moreover, an optical intensity calculating device 23B, for inputting the current that has been amplified by the amplifier 21B to calculate the intensity of the light detected by the second photodetecting element 20B, is connected to the amplifier 21B. An optical intensity storing device 24B for saving the optical intensity calculated by the optical intensity calculating device 23B is connected to the optical intensity calculating device 23B.

A scattered light measuring instrument 105 detects scattered light that is produced by microorganisms, non-microorganism particles, and bubbles that are illuminated with the inspection beam. The scattered light measuring instrument 105 comprises a scattered light photodetecting element 50 for detecting scattered light. A photodiode, or the like, may be used for the scattered light photodetecting element 50, to convert optical energy into electrical energy when light is detected.

An amplifier 51 for amplifying the electric current that is produced by the scattered light photodetecting element 50 is connected to the scattered light photodetecting element 50. An amplifier power supply 52 for supplying electric power to the amplifier 51 is connected to the amplifier 51. Moreover, an optical intensity calculating device 53, for inputting the current that has been amplified by the amplifier 51 to calculate the intensity of the scattered light detected by the scattered light photodetecting element 50, is connected to the amplifier 51. An optical intensity storing device 54 for saving the intensity of scattered light calculated by the optical intensity calculating device 53 is connected to the optical intensity calculating device 53.

Figure 3:
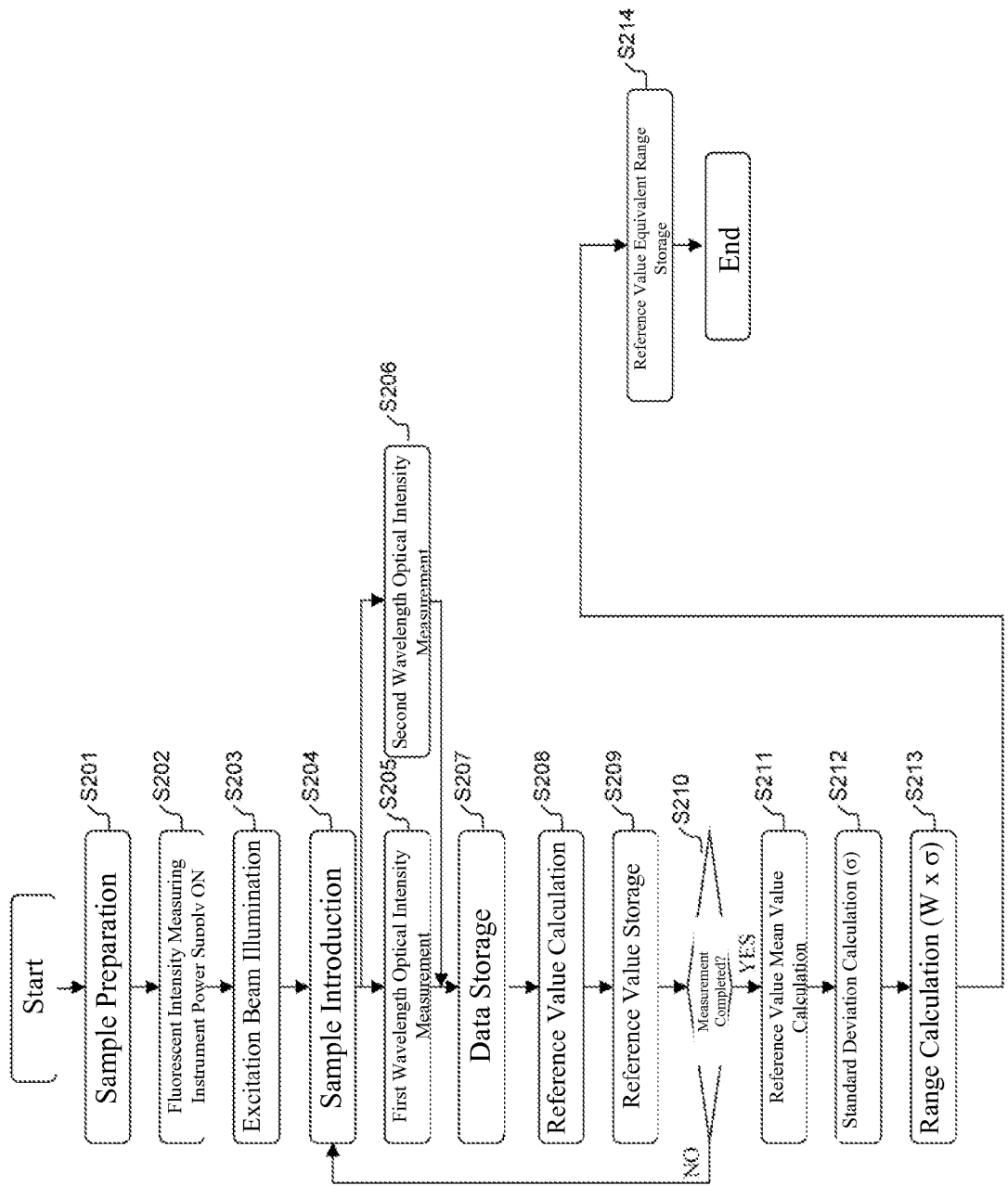
FIG. 3 is a flowchart illustrating a method for obtaining a reference value as set forth in the Example according to the present disclosure.

The method for acquiring, as a reference value, a relative value for the light intensities of the fluorescent band emitted by a prescribed substance illuminated with the inspection beam, measured at at least two wavelengths and saved in the reference value storing device 351 will be explained next using the flow chart of FIG. 3. Note that here the explanation will be for an example wherein the prescribed substance that is illuminated by the inspection beam is a prescribed microorganism that may occur in the purified water manufacturing device 100 that is the subject of detection by the detecting device 20.

In Step S201, a prescribed microorganism is prepared. Purified water wherein contaminants have been illuminated is prepared as well, and the microorganisms are introduced therein. In Step S202, the power supply to the fluorescent intensity measuring instrument 102, illustrated in FIG. 2, is turned ON, and in Step S203, the inspection beam is emitted from the light source 10. Following this, in Step S204, the flow of the purified water that includes the microorganisms is directed to the focal point of the inspection beam. In Step S205, the fluorescent intensity measuring instrument 102 uses the first photodetecting element 20A to measure the fluorescent intensity at the first wavelength. Additionally, at the same time as Step S205, in Step S206 the fluorescent intensity measuring instrument 102 uses the second photodetecting element 20B to measure the fluorescent intensity at the second wavelength.

In Step S207, the fluorescent intensity measuring instrument 102 saves the fluorescent intensity at the first wavelength and the fluorescent intensity at the second wavelength, derived from the microorganisms, into the optical intensity storing devices 24A and 24B. In Step S208, the relative value calculating portion 303 reads out, from the optical intensity storing devices 24A and 24B, the value for the fluorescent intensity at the first wavelength and the value for the fluorescent intensity at the second wavelength and, for example, divides the value of the fluorescent intensity at the first wavelength by the value for the fluorescent intensity at the second wavelength, to calculate a reference value. In Step S209, the reference value calculating portion 303 saves the calculated reference value into the reference value storing device 351. In Step S210, the reference value calculating portion 303 evaluates whether or not the calculation of reference values has been completed. If, for example, there is the need to acquire reference values multiple times to calculate a mean, the relative value calculating portion 303 evaluates whether or not the number of reference values required for calculating the mean has been acquired. If the number of reference values required for calculating the mean has not been acquired, then processing returns to Step S204. If the number of reference values required for calculating the mean has been acquired, then processing advances to Step S211.

In Step S211, the relative value calculating portion 303 reads out a plurality of reference values from the reference value storing device 351, to calculate the mean of the reference values. In Step S212, the relative value calculating portion 303 calculates a standard deviation σ for the reference values. Furthermore, in Step S212, the relative value calculating portion 303 calculates the value Wσ by multiplying by a prescribed constant W the standard deviation σ of the reference value. The relative value calculating portion 303 defines, as an equivalent range, the range from the reference value−Wσ/2 to the reference value+Wσ/2, and in Step S214 saves it in the reference value storing device 351. For example, through the method described above, a reference value for a prescribed microorganism, and an equivalent range for the reference value, are stored in the reference value storing device 351. Note that reference values and reference value equivalent ranges may be stored in the reference value storing device 351 for a plurality of microorganisms.

Moreover, through a similar method, a relative value for the light intensity produced by a prescribed non-microorganism particle that is illuminated by an inspection beam is acquired as a reference value and stored in the reference value storing device 351. Moreover, reference values and equivalent ranges for reference values may be stored in the reference value storing device 351 for a plurality of non-microorganism particles.

The spectra of light in the fluorescent band emitted by microorganism and non-microorganism particles will differ depending on the type of microorganism or non-microorganism particle. Moreover, typically the light intensity in the fluorescent band emitted by a microorganism tends to be stronger than the intensity of light in the fluorescent band emitted by a non-microorganism particle. Because of that, it is possible to differentiate a microorganism versus a non-microorganism particle included in the water based on the intensity of light in the fluorescent band detected at a plurality of wavelengths.

When the detecting device 20 illustrated in FIG. 1 begins drawing water that is being manufactured by the purified water manufacturing device 100 or water that has been manufactured by the purified water manufacturing device 100, the light source 10, shown in FIG. 2, illuminates the drawn water with the inspection beam, the fluorescent intensity measuring instrument 102 measures, and stores in the optical intensity storing devices 24A and 24B, the intensity of light in the fluorescent band at the first wavelength and the intensity of light in the fluorescent band at the second wavelength. Moreover, the scattered light measuring instrument 105 measures, and stores in the optical intensity storing device 54, the optical intensity of the scattered light.

In the detecting device 20 according to the Example, the CPU 300 further includes a scattered light reference evaluating portion 305. The scattered light reference evaluating portion 305 reads out the value for the intensity of light in the fluorescent band at the first wavelength and the value of the intensity of light in the fluorescent band from the second wavelength from the optical intensity storing devices 24A and 24B. The scattered light reference evaluating portion 305 also reads out the intensity of scattered light from the optical intensity storing device 54.

The scattered light reference evaluating portion 305 evaluates that the water that is subject to inspection includes a bubble when the scattered light measuring instrument 105 has measured scattered light but the fluorescent intensity measuring instrument 102 has not measured light in the fluorescent band. Moreover, the scattered light reference evaluating portion 305 may also evaluate that the water that is subject to inspection does not include a microorganism or a non-microorganism particle if the scattered light measuring instrument 105 has measured scattered light that the fluorescent intensity measuring instrument 102 has not measured light in the fluorescent band. Moreover, the scattered light reference evaluating portion 305 may evaluate that the water that is subject to inspection includes a microorganism or a non-microorganism particle if the fluorescent intensity measuring instrument 102 has measured light in the fluorescent band and the scattered light measuring instrument 105 has measured scattered light.

The relative value calculating portion 303 reads out, from the optical intensity storing devices 24A and 24B, the value for the intensity of light at the first wavelength and the value for the intensity of light at the second wavelength. Moreover, the relative value calculating portion 303 divides the value for the intensity of light at the first wavelength by the value for the intensity of light at the second wavelength to calculate a relative value. Note that the method for calculating the relative value is the same as the method for calculating the reference value. The relative value calculating portion 303 saves the calculated relative value into a relative value storing device 352 that is connected to the CPU 300.

The comparison evaluating portion 304 reads out the calculated relative value from the relative value storing device 352 and reads out the equivalent range for the reference value for a prescribed microorganism from the reference value storing device 351. Following this, the comparison evaluating portion 304 evaluates whether or not the calculated relative value is within the equivalent range for the reference value for the prescribed microorganism. If the calculated relative value is within the equivalent range for the reference value for the prescribed microorganism, then the comparison evaluating portion 304 evaluates that the water includes the prescribed microorganism. Moreover, if the calculated relative value is not included in the equivalent range for the reference value for the prescribed microorganism, the comparison evaluating portion 304 evaluates that the water does not include the prescribed microorganism.

When equivalent ranges of reference values for a plurality of prescribed microorganisms are saved in the reference value storing device 351, the comparison evaluating portion 304 evaluates whether or not the calculated relative value is included in the respective equivalent ranges for the reference values for each of the plurality of prescribed microorganisms.

Moreover, the comparison evaluating portion 304 reads out, from the reference value storing device 351, the equivalent range for the reference value for the prescribed non-microorganism particle. Following this, the comparison evaluating portion 304 evaluates whether or not the calculated relative value is within the equivalent range for the reference value for the prescribed non-microorganism particle. If the calculated relative value is within the equivalent range for the reference value for the prescribed non-microorganism particle, then the comparison evaluating portion 304 evaluates that the water includes the prescribed non-microorganism particle. Moreover, if the calculated relative value is not included in the equivalent range for the reference value for the prescribed non-microorganism particle, the comparison evaluating portion 304 evaluates that the water does not include the prescribed non-microorganism particle.

When equivalent ranges of reference values for a plurality of prescribed non-microorganism particles are saved in the reference value storing device 351, the comparison evaluating portion 304 evaluates whether or not the calculated relative value is included in the respective equivalent ranges for the reference values for each of the plurality of prescribed non-microorganism particles.

The measured value specifying portion 301 specifies measured values for the respective numbers of microorganisms, non-microorganism particles, and bubbles evaluated by the comparison evaluating portion 304 and the scattered light reference evaluating portion 305 included in the water. For example, the measured value specifying portion 301 specifies measured values for the respective numbers of microorganisms, non-microorganism particles, and bubbles included in the water based on the number of times scattered light or fluorescence is detected within a prescribed time interval or a prescribed volume of water. Conversely, the measured value specifying portion 301 specifies measured values for the respective numbers of microorganisms, non-microorganism particles, and bubbles included in the water based on cumulative values of detected intensities of scattered light or fluorescence over a prescribed time interval or for a prescribed volume of water. Here the measured values for the respective numbers of microorganisms, non-microorganism particles, and bubbles includes measured values for respective densities of microorganisms, non-microorganism particles, and bubbles included in the water.

For example, the respective numbers of microorganisms, non-microorganism particles, and bubbles included in a prescribed volume of water for the water flowing in the main pipe 1 can be specified from the respective numbers of microorganisms, non-microorganism particles, and bubbles included in water of a prescribed volume in the water that flows in the branch flow pipe 2, and the flow rate ratio between the flow rate of the water that flows in the main pipe 1 and the flow rate of the water that flows in the branch flow pipe 2. The respective flow rates of the water that flows in the main pipe 1 and the water that flows in the branch flow pipe 2 can be measured using flow meters.

An evaluation standard storing device 353 is connected to the CPU 300. The evaluation standard storing device 353 saves prescribed standard values for issuing warnings that a number of microorganisms, for example that is larger than that are included in the water. Note that the evaluation standard storing device 353 may store multiple prescribed standard values regarding the number of microorganisms. For example, the evaluation standard storing device 353 may store a prescribed standard value wherein handling can be through running a germicide or solvent through the purified water manufacturing device 100, and a prescribed standard value that requires replacement of a filter that is provided in the purified water manufacturing device 100.

Moreover, the evaluation standard storing device 353 saves prescribed standard values for issuing warnings that a number of non-microorganism particles, for example that is larger than that are included in the water. Note that the evaluation standard storing device 353 may store multiple prescribed standard values regarding the number of non-microorganism particles. For example, the evaluation standard storing device 353 may store a prescribed standard value wherein handling can be through cleaning the filter in the purified water manufacturing device 100, and a prescribed standard value that requires replacement of a filter that is provided in the purified water manufacturing device 100.

The state evaluating portion 302 compares the measured value for the number of microorganisms included within the water, specified by the measured value specifying portion 301, and a prescribed standard value for the microorganisms, stored in the evaluation standard storing device 353. If the measured value for the number of microorganisms included in the water is greater than the prescribed standard value, then the evaluation is that a problem has occurred in the purified water manufacturing device 100, producing microorganisms in excess of the standard value. Moreover, the state evaluating portion 302 issues a warning through an outputting device 401, or the like, to the effect that there are microorganisms in excess of the standard value. In this case, for example, one may consider that microorganisms trapped in a filter provided in the purified water manufacturing device are propagating, that a biofilm has been formed, or that microorganisms are passing through the filters. This may be handled, for example, by running a germicide or a solvent through the purified water manufacturing device 100. See, for example, International Patent Application Publication No. 2008/038575. Conversely, this may also be handled by replacing the filter in the purified water manufacturing device 100.

Moreover, the state evaluating portion 302 compares the measured value for the number of non-microorganism particles included within the water, specified by the measured value specifying portion 301, and a prescribed standard value for the non-microorganism particles, stored in the evaluation standard storing device 353. If the measured value for the number of non-microorganism particles included in the water is greater than the prescribed standard value, then the evaluation is that a problem has occurred in the purified water manufacturing device 100, producing non-microorganism particles in excess of the standard value. Moreover, the state evaluating portion 302 issues a warning through an outputting device 401, or the like, to the effect that there are non-microorganism particles in excess of the standard value. In this case, for example, one may consider that non-microorganism particles have accumulated in the filter provided in the purified water manufacturing device 100, or that non-microorganism particles are passing through the filters. For this, this may be handled, for example, by cleaning or replacing the filter in the purified water manufacturing device 100.

A display, a speaker, a printer, or the like, may be used for the outputting device 401.

The purified water manufacturing device monitoring system according to the Example, set forth above, enables the state of the purified water manufacturing device 100 to be monitored in real time. Moreover, it enables discrimination between microorganisms and non-microorganism particles included in the water. It also enables non-microorganism particles to be discriminated from bubbles.

Another Example

Figure 4:
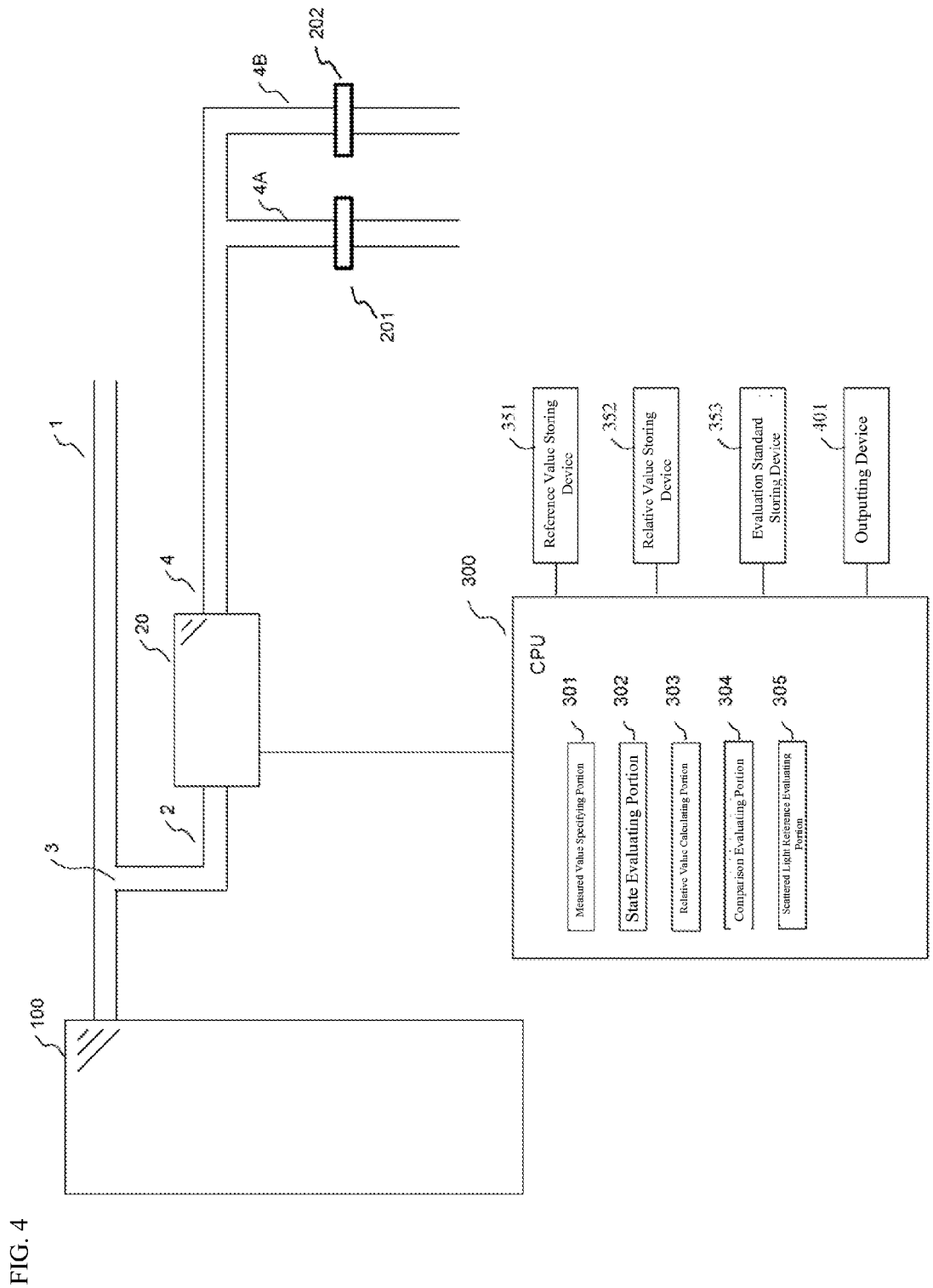
FIG. 4 is a schematic diagram of a purified water manufacturing apparatus monitoring system as set forth in Another Example according to the present disclosure.

In a purified water manufacturing device monitoring system according to Another Example, as illustrated in FIG. 4, the drain pipe 4 that is the flow path for the water after being illuminated by the inspection beam is split into two drainpipes 4A and 4B. A microorganism filter 201 that is able to trap microorganisms is provided in the drain pipe 4A. A mixture of ester, polyvinylidene fluoride (PVDF), polyether sulfone, and the like, with cellulose may be used as the material for the microorganism filter 201. A non-microorganism particle filter 202 that is able to trap non-microorganism particles is provided in the drain pipe 4B. Polycarbonate or a metal such as silver, or the like, for example, may be used as the material for the non-microorganism particle filter 202.

The microorganisms trapped in the microorganism filter 201 can be cultured and observed to verify the types and numbers of microorganisms detected by the purified water manufacturing device monitoring system. When culturing bacterial microorganisms, a tryptic soy agar (TSA) culture medium, an R2A culture medium, or a standard agar culture medium, or the like, may be used as the culture medium. Bacterial microorganisms are cultured, for example, for seven days at 32° C. When culturing fungal microorganisms, a potato glucose agar (PDA) culture medium, a Sabouraud agar culture medium, or the like, may be used. Fungal microorganisms are cultured at, for example, for seven days at 25° C. When culturing the microorganisms, the microorganism filter 201 that has trapped the microorganisms may be brought into contact with the culture medium, or the microorganisms may be recovered from the microorganism filter 201 and the recovered microorganisms may be placed into the culture medium.

Moreover, the non-microorganism particles trapped in the non-microorganism particle filter 202 can be observed to verify the types and numbers of non-microorganism particles detected by the purified water manufacturing device monitoring system. The non-microorganism particles trapped in the non-microorganism particle filter 202 may be observed using an optical microscope, a phase difference microscope, a fluorescent microscope, or an electron microscope.

Yet Another Example

Figure 5:
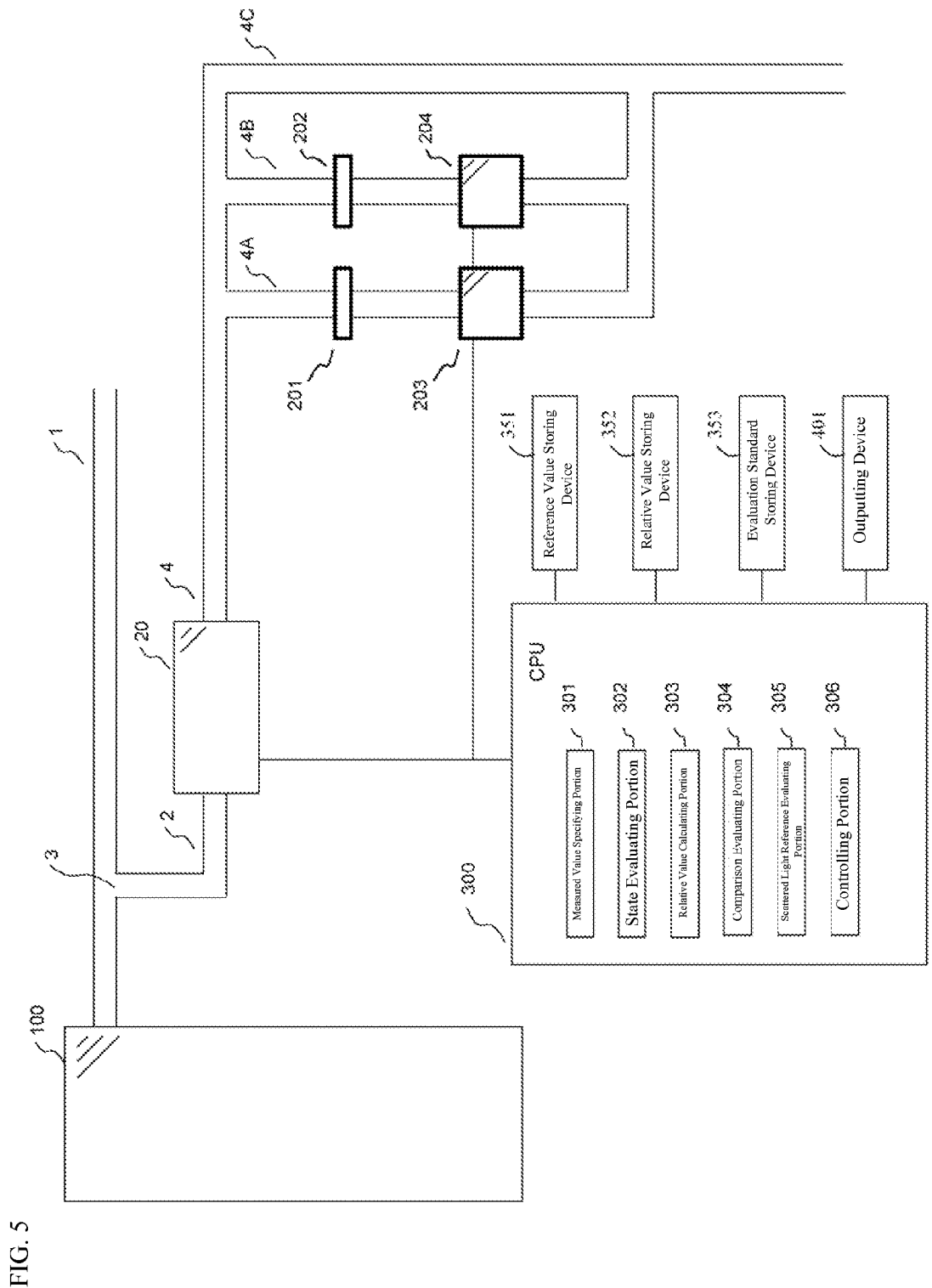
FIG. 5 is a schematic diagram of a purified water manufacturing apparatus monitoring system as set forth in Yet Another Example according to the present disclosure.

In a purified water manufacturing device monitoring system according to Yet Another Example, as illustrated in FIG. 5, the drain pipe 4 is split into three drainpipes 4A, 4B, and 4C. A microorganism filter 201 that is able to trap microorganisms, and a suction pump 203, are provided in the drain pipe 4A. A non-microorganism particle filter 202 that can trap non-microorganism particles, and a suction pump 204, are provided in the drain pump 4B. The suction pumps 203 and 204 may, for example, be connected electrically to the CPU 300.

In the Yet Another Example, the CPU 300 further comprises a controlling portion 306. When the comparison evaluating portion 304 evaluates that a microorganism is included in the water, the controlling portion 306 drives the suction pump 203 to direct the water into the drainpipe 4A after illumination with the inspection beam. This causes the microorganism within the water to be trapped in the microorganism filter 201. Moreover, when the comparison evaluating portion 304 evaluates that a non-microorganism particle is included in the water, the controlling portion 306 drives the suction pump 204 to direct the water into the drainpipe 4B after illumination with the inspection beam. This causes the non-microorganism particle within the water to be trapped in the non-microorganism particle filter 202. The trapped microorganism or non-microorganism particle can be observed to verify the types and numbers of microorganisms and non-microorganism particles detected by the purified water manufacturing device monitoring system.

Further Example

Figure 6:
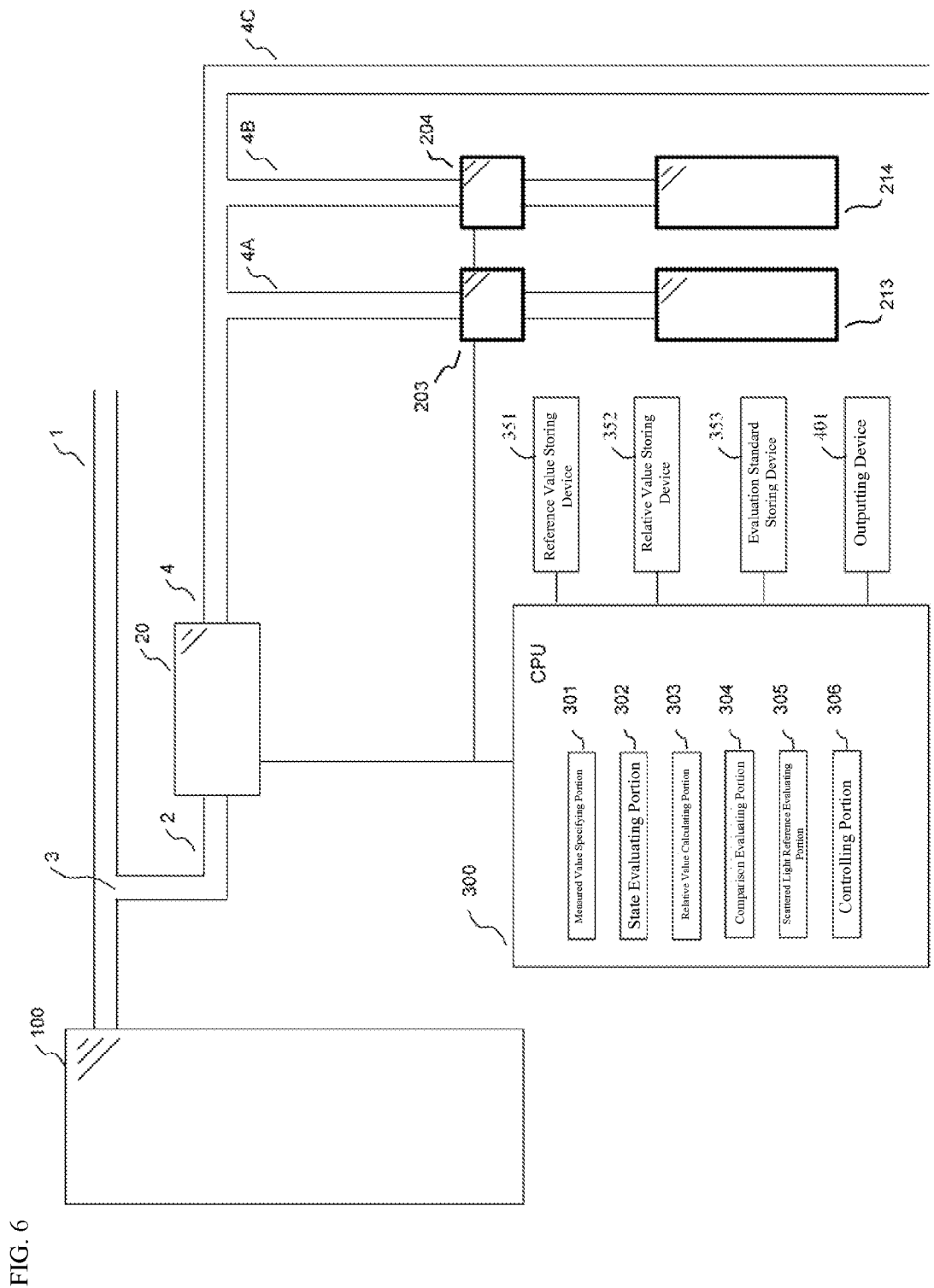
FIG. 6 is a schematic diagram of a purified water manufacturing apparatus monitoring system as set forth in Further Example according to the present disclosure.

In a purified water manufacturing device monitoring system according to Further Example, as illustrated in FIG. 6, a suction pump 203 and a waste fluid tank 213 are provided on the drainpipe 4A. A suction pump 204 and a waste fluid tank 214 are provided on the drain pipe 4B.

When the comparison evaluating portion 304 of the CPU 300 evaluates that the water includes a microorganism, the controlling portion 306 drives the suction pump 203 to guide the water after illumination by the inspection beam into the drain pump 4A, to store, in the waste fluid tank 213, the water that includes the microorganisms. This causes the water that includes the microorganisms to be stored in the waste fluid tank 213. Moreover, when the comparison evaluating portion 304 evaluates that a non-microorganism particle is included in the water, the controlling portion 306 drives the suction pump 204 to direct the water into the drainpipe 4B after illumination with the inspection beam. This causes the water that includes the non-microorganism particles to be stored in the waste fluid tank 214. The microorganisms within the water that is stored in the waste fluid tank 213 or the non-microorganism particles within the water that is stored in the waste fluid tank 214 can be observed to verify the types and numbers of microorganisms and non-microorganism particles detected by the purified water manufacturing device monitoring system.

Another Further Example

Figure 7:
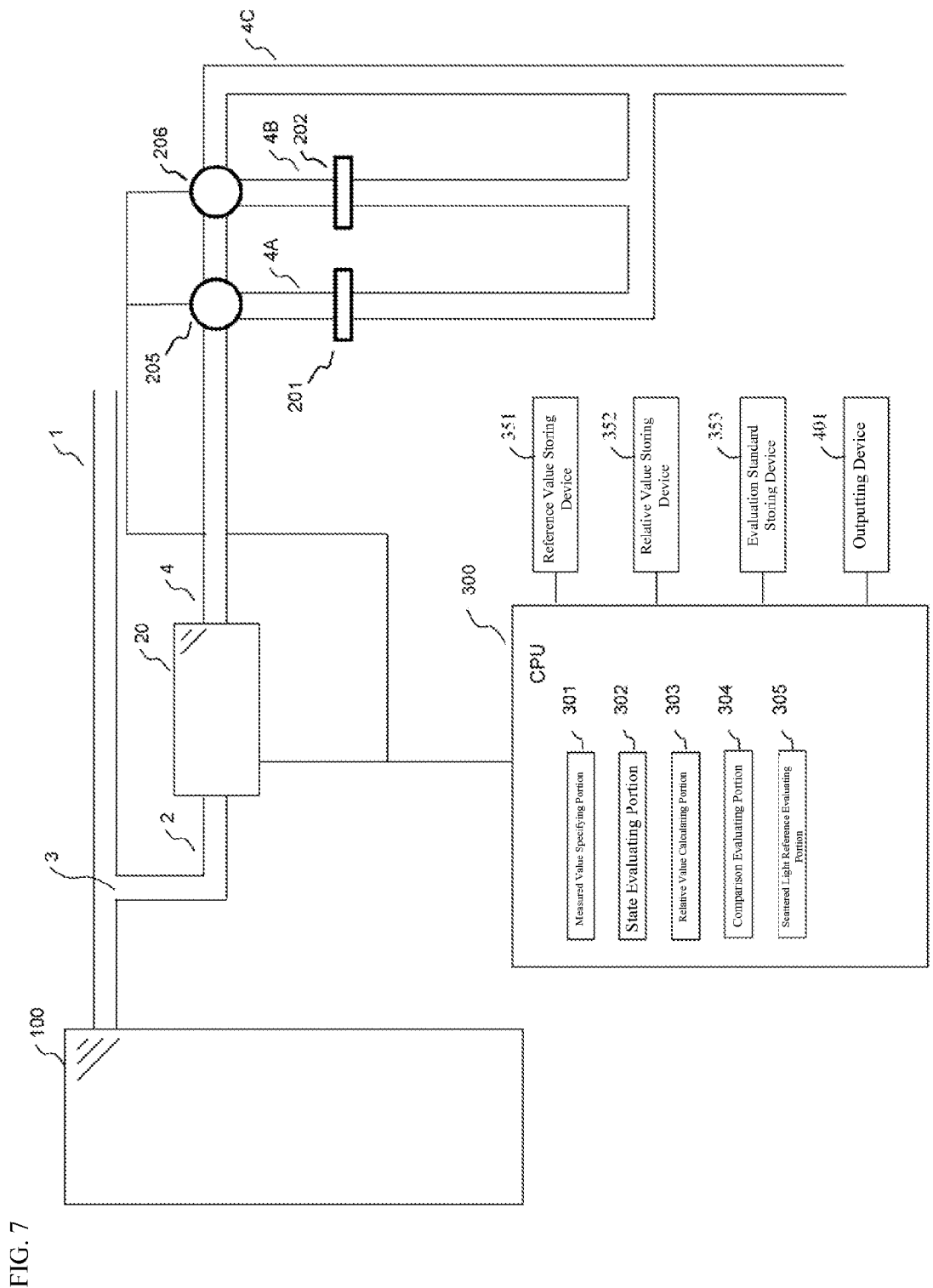
FIG. 7 is a schematic diagram of a purified water manufacturing apparatus monitoring system as set forth in Another Further Example according to the present disclosure.

In the purified water manufacturing device monitoring system according to Another Further Example, as illustrated in FIG. 7, a valve 205 is provided at the place wherein the drainpipe 4 and the drain pipe 4A branch. A valve 206 is provided at the place wherein the drainpipe 4 and the drainpipe 4B branch. The valves 205 and 206 may be connected electrically to the CPU 300, for example. A microorganism filter 201 that is able to trap microorganisms is provided in the drain pipe 4A. A non-microorganism particle filter 202 that is able to trap non-microorganism particles is provided in the drain pipe 4B.

When the comparison evaluating portion 304 of the CPU 300 evaluates that a microorganism is included in the water, the controlling portion 306 drives the valve 205 to direct the water into the drainpipe 4A after illumination with the inspection beam. This causes the microorganism within the water to be trapped in the microorganism filter 201. Moreover, when the comparison evaluating portion 304 evaluates that a non-microorganism particle is included in the water, the controlling portion 306 drives the valve 206 to direct the water into the drainpipe 4B after illumination with the inspection beam. This causes the non-microorganism particle within the water to be trapped in the non-microorganism particle filter 202. The trapped microorganism or non-microorganism particle can be observed to verify the types and numbers of microorganisms and non-microorganism particles detected by the purified water manufacturing device monitoring system.

Yet Another Further Example

Figure 8:
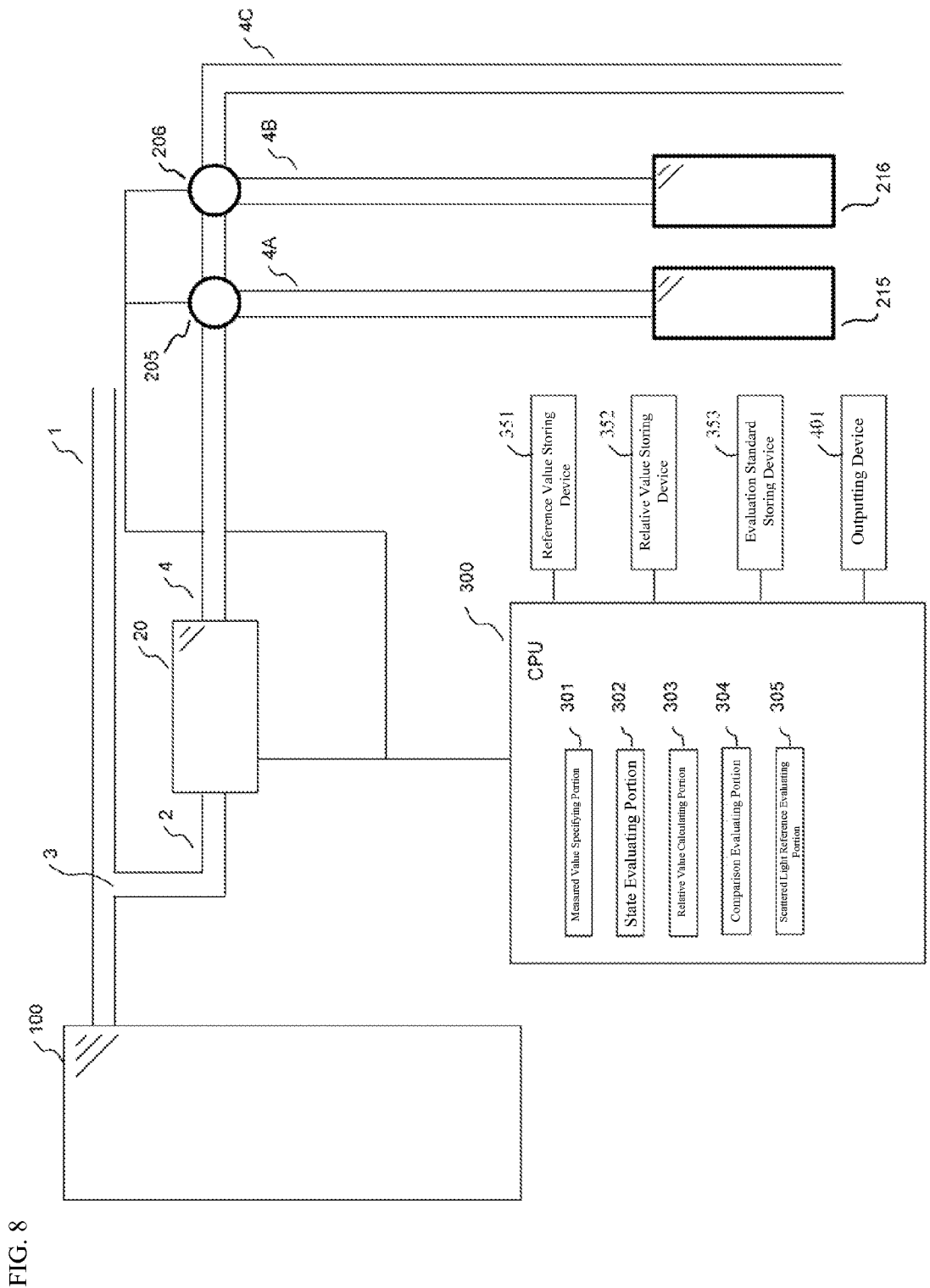
FIG. 8 is a schematic diagram of a purified water manufacturing apparatus monitoring system as set forth in Yet Another Further Example according to the present disclosure.

In the purified water manufacturing device monitoring system according to Yet Another Further Example, as illustrated in FIG. 8, a waste fluid tank 215 is provided on the drainpipe 4A. A waste fluid tank 216 is provided on the drainpipe 4B.

When the comparison evaluating portion 304 of the CPU 300 evaluates that a microorganism is included in the water, the controlling portion 306 drives the valve 205 to direct the water into the drainpipe 4A after illumination with the inspection beam. This causes the water that includes the microorganisms to be stored in the waste fluid tank 215. Moreover, when the comparison evaluating portion 304 evaluates that a non-microorganism particle is included in the water, the controlling portion 306 drives the valve 206 to direct the water into the drainpipe 4B after illumination with the inspection beam. This causes the water that includes the non-microorganism particles to be stored in the waste fluid tank 216. The microorganisms within the water that is stored in the waste fluid tank 215 or the non-microorganism particles within the water that is stored in the waste fluid tank 216 can be observed to verify the types and numbers of microorganisms and non-microorganism particles detected by the purified water manufacturing device monitoring system.

Other Examples

While there are descriptions of examples as set forth above, the descriptions and drawings that form a portion of the disclosure are not to be understood to limit the present disclosure. A variety of alternate examples and operating technologies should be obvious to those skilled in the art. For example, the method for identifying whether the particle that is included in the water is a microorganism, is a non-microorganism, or is a bubble is not limited to the method described above. For example, the intensity of the light that is scattered from the particles is correlated to the diameters of the particles. Moreover, the sizes of the microorganisms and non-microorganism particles vary depending on the type of microorganism and non-microorganism particle. Because of this, the type of microorganism or non-microorganism particle included in the water may be identified from the intensity of the scattered light that is detected. The methods disclosed in U.S. Pat. No. 6,885,440 and U.S. Pat. No. 7,106,442 may be used as other methods by which to identify the type of particle. In this way, the present disclosure should be understood to include a variety of examples, and the like, not set forth herein.

Although there is no limitation to the below, the present invention may be used on a manufacturing work floor for manufacturing purified water for pharmaceuticals, purified water for foodstuffs, purified water for beverages, purified water for semiconductor device manufacturing, and the like.

The invention claimed is:

1. A purified water manufacturing device monitoring system, comprising:
    a detecting device that illuminates, with an inspection beam, water either that is in a process of being manufactured or that has been manufactured by a purified water manufacturing device, detects light in a region illuminated by the inspection beam, and detects a microorganism or a non-microorganism particle included in the water;
    a measured value specifier that specifies a measured value for a number of microorganisms detected and specifies a measured value for a number of non-microorganism particles detected;
    a state evaluator that evaluates that a problem has occurred in the purified water manufacturing device when either or both the measured value for the number of microorganisms and the measured value for the number of non-microorganism particles are greater than a prescribed value; and
    a first flow path and a second flow path downstream from the inspection beam wherein the system is configured to divert water from the first flow path to the second flow path when the state evaluator evaluates that a problem has occurred in the purified water manufacturing device;
    wherein the second flow path is configured to trap at least one of microorganisms and non-microorganism particles.

2. The purified water manufacturing device monitoring system as set forth in claim 1, wherein:
    the light produced in the region wherein the water is illuminated with the inspection beam is scattered light.

3. The purified water manufacturing device monitoring system as set forth in claim 1, wherein:
    the light produced in the region wherein the water is illuminated with the inspection beam is fluorescent light.

4. The purified water manufacturing device monitoring system as set forth in claim 1, wherein:
    the non-microorganism particle includes a bubble.

5. The purified water manufacturing device monitoring system as set forth in claim 4, wherein:
    the non-microorganism particle and the bubble are discriminated based on an intensity of fluorescence.

6. The purified water manufacturing device monitoring system as set forth in claim 1, wherein:
    the detecting device measures, at at least two wavelengths, intensities of light in a fluorescent band produced at the region illuminated by the inspection beam; and
    the detecting device further comprises:
        a relative value calculator that calculates a relative value of the intensities of light measured at the at least two wavelengths;
        a reference value storing device that stores, as a reference value, a relative value for the intensities of light produced by a prescribed substance illuminated by the inspection beam, measured at at least two wavelengths; and
        a comparison evaluator that compares the calculated relative value and the reference value, as the prescribed value, to evaluate whether or not the water includes the microorganism or the non-microorganism particle.

7. The purified water manufacturing device monitoring system as set forth in claim 1, wherein:
    the water is water for pharmaceutical manufacturing.

8. The purified water manufacturing device monitoring system as set forth in claim 1, further comprising:
    a microorganism filter that traps the microorganism, provided in the second flow path.

9. The purified water manufacturing device monitoring system as set forth in claim 1, further comprising:
    a non-microorganism particle filter that traps the non-microorganism particle, provided in the second flow path.

10. A purified water manufacturing device monitoring method, comprising:
    illuminating, with an inspection beam, water either that is in a process of being manufactured or that has been manufactured by a purified water manufacturing device, and detecting light in a region illuminated by the inspection beam to detect a microorganism or a non-microorganism particle included in the water;

specifying a measured value for a number of microorganisms detected and for specifying a measured value for a number of non-microorganism particles detected;

evaluating that a problem has occurred in the purified water manufacturing device when either or both the measured value for the number of microorganisms and the measured value for the number of non-microorganism particles are greater than a prescribed value; and diverting the water from a first flow path downstream from the inspection beam to a second flow path downstream from the inspection beam in response to an evaluation that a problem has occurred in the purified water manufacturing device;

wherein the second flow path is configured to trap at least one of microorganisms and non-microorganism particles.

11. The purified water manufacturing device monitoring method as set forth in claim 10, wherein:

the light produced in the region wherein the water is illuminated with the inspection beam is scattered light.

12. The purified water manufacturing device monitoring method as set forth in claim 10, wherein:

the light produced in the region wherein the water is illuminated with the inspection beam is fluorescent light.

13. The purified water manufacturing device monitoring method as set forth in claim 10, wherein:

the non-microorganism particle includes a bubble.

14. The purified water manufacturing device monitoring method as set forth in claim 13, wherein:

the non-microorganism particle and the bubble are discriminated based on an intensity of fluorescence.

15. The purified water manufacturing device monitoring method as set forth in claim 10, wherein:

at at least two wavelengths, intensities of light in a fluorescent band produced at the region illuminated by the inspection beam are measured in the detection; and the method further comprising:

calculating a relative value of the intensities of light measured at the at least two wavelengths;

preparing, as a reference value, a relative value for the intensities of light produced by a prescribed substance illuminated by the inspection beam, measured at at least two wavelengths in advance; and comparing the calculated relative value and the reference value, as the prescribed value, to evaluate whether or not the water includes the microorganism or the non-microorganism particle.

16. The purified water manufacturing device monitoring method as set forth in claim 10, wherein:

the water is water for pharmaceutical manufacturing.

17. The purified water manufacturing device monitoring method as set forth in claim 10, further comprising:

evaluating that a biofilm has formed in the purified water manufacturing device when the measured value for the number of microorganisms is greater than a prescribed value.

18. The purified water manufacturing device monitoring method as set forth in claim 10, further comprising:

evaluating that non-microorganism particles have accumulated in the purified water manufacturing device when the measured value for the number of non-microorganism particles is greater than a prescribed value.

19. The purified water manufacturing device monitoring method as set claim 10, further comprising:

trapping the microorganism in a microorganism filter provided in the second flow path.

20. The purified water manufacturing device monitoring method as set forth in claim 19, further comprising:

culturing the microorganism trapped by the microorganism filter.

21. The purified water manufacturing device monitoring system as set forth in claim 8, further comprising:

a third flow path downstream from the inspection beam; and a non-microorganism filter that traps the non-microorganism particle, provided in the third flow path;

wherein the system is configured to divert water from the first flow path to the second flow path when the state evaluator evaluates that the measured value for the number of microorganisms is greater than a first prescribed value; and wherein the system is configured to divert water from the first flow path to the third flow path when the state evaluator evaluates that the measured value for the number of non-microorganism particles is greater than a second prescribed value.

22. The purified water manufacturing device monitoring method as set forth in claim 19, further comprising:

diverting the water from the first flow path downstream from the inspection beam to the second flow path downstream from the inspection beam in response to an evaluation that the measured value for the number of microorganisms is greater than a first prescribed value; and diverting the water from the first flow path downstream from the inspection beam to a third flow path downstream from the inspection beam in response to an evaluation that the measured value for the number of non-microorganism particles is greater than a second prescribed value and trapping the non-microorganism particles in a non-microorganism filter provided in the third flow path.

* * * * *